(12) United States Patent
Bai

(10) Patent No.: US 8,456,630 B2
(45) Date of Patent: Jun. 4, 2013

(54) FIBER BASED SERS SENSOR

(75) Inventor: Shuang Bai, Sunnyvale, CA (US)

(73) Assignee: PolarOnyx, Inc., San Jose, CA (US)

( * ) Notice: Subject to any disclaimer, the term of this patent is extended or adjusted under 35 U.S.C. 154(b) by 195 days.

(21) Appl. No.: 13/103,030

(22) Filed: May 6, 2011

(65) Prior Publication Data

US 2012/0281209 A1    Nov. 8, 2012

(51) Int. Cl.
*G01J 3/44* (2006.01)

(52) U.S. Cl.
USPC .......................................... 356/301; 356/326

(58) Field of Classification Search
USPC ........................... 356/301, 326; 385/123, 126
See application file for complete search history.

(56) References Cited

U.S. PATENT DOCUMENTS

| 7,110,109 | B2 * | 9/2006 | Knopp et al. | 356/301 |
| 7,738,097 | B2 * | 6/2010 | Khetani et al. | 356/301 |
| 2007/0020144 | A1 * | 1/2007 | Du et al. | 422/58 |
| 2011/0176130 | A1 * | 7/2011 | Gu et al. | 356/301 |
| 2011/0267612 | A1 * | 11/2011 | Roberts et al. | 356/301 |

OTHER PUBLICATIONS

O. S. Wolfbeis, "Fiber-Optic Chemical Sensors and Biosensors," Anal. Chem., 80(12):4269, 2008.
T. Vo-Dinh and P. M. Kasili, "Fiber-optic nanosensors for single-cell monitoring," Anal. Bioanal. Chem., 382:918, 2005.
D. L. Stokes, Z. H. Chi, and T. Vo-Dinh, "Surface-Enhanced-Raman-Scattering-Inducing Nanoprobe for Spectrochemical Analysis," Appl. Spectrosc., 58(3):292, 2004.
D. L. Stokes and T. Vo-Dinh, "Development of an integrated single-fiber SERS sensor," Sens. Actuators B, 69:28, 2000.
R. Gessner, P. Rosch, R. Petry, M. Schmitt, M. A. Strehle, W. Kiefer, and J. Popp, "The application of a SERS fiber probe for the investigation of sensitive biological samples," Analyst, 129:1193, 2004.
A. Campion and P. Kambhampati, "Surface-enhanced Raman scattering," Chem. Soc. Rev., 27:241, 1998.
K. Kneipp, H. Kneipp, I. Itzkan, R. R. Dasari, and M. S. Feld, "Surface-enhanced Raman scattering and biophysics," J. Phys. Cond. Mat., 14(18):R597, 2002.
A. Otto, I. Mrozek, H. Grabhorn, and W. Akemann, "Surface-enhanced Raman scattering," J. Phys. Cond. Mat., 4 (5):1143, 1992.
Y. Zhang, C. Gu, A. M. Schwartzberg, and J. Z. Zhang, "Surface-enhanced Raman scattering sensor based on D-shaped fiber," Appl. Phys. Lett., 87:123105, 2005.

(Continued)

*Primary Examiner* — Layla Lauchman
(74) *Attorney, Agent, or Firm* — Taboada Law Firm, PLLC; John M. Taboada

(57) ABSTRACT

Methods and systems for enhanced SERS sensing are disclosed, including generating electromagnetic radiation from a fiber laser; coupling the radiation to a SERS sensor comprising: a fiber comprising a first end and a second end, wherein the first end is coupled to the fiber laser and the second end is deposited with one or more metal nanoparticles; an in-line fiber grating integrated into the fiber between the first and the second end; a spectrometer configured to measure a spectrum produced by the in-line fiber grating; and a micro-processor configured to control the fiber laser and the spectrometer; exciting one or more molecules adsorbed on the surface of the one or more metal nanoparticles to generate a Raman signal; coupling the signal into the fiber; separating the signal into its wavelength components with the in-line fiber grating; and measuring the wavelength components with the spectrometer. Other embodiments are described and claimed.

20 Claims, 15 Drawing Sheets

OTHER PUBLICATIONS

C. Gu, Y. Y. Zhang, A. M. Schwartzberg, and J. Z. Zhang, "Ultra-sensitive Compact Fiber Sensor Based on Nanoparticle Surface Enhanced Raman Scattering," SPIE Proc., 5911:591108, 2005.

Y. Zhang, C. Gu, A. M. Schwartzberg, and J. Z. Zhang, Single-Fiber Probe Based on Surface Enhanced Raman Scattering (SERS). IEEE Sensors, p. 1088, 2005.

Y. Zhang, C. Shi, C. Gu, L. Seballos, and J. Z. Zhang, "Liquid core photonic crystal fiber sensor based on surface enhanced Raman scattering," Appl. Phys. Lett., 90:193504, 2007.

H. Yan, C. Gu, C. Yang, J. Liu, G. Jin, J. Zhang, L. Hou, and Y. Yao, "Hollow core photonic crystal fiber surface-enhanced Raman probe," Appl. Phys. Lett., 89:204101, 2006.

Y. Zhu, H. Du, and R. Bise, "Design of solid-core microstructured optical fiber with steering-wheel air cladding for optimal evanescent-field sensing," Opt. Exp., 14(8):3541, 2006.

D. Pristinski, S. Tan, M. Erol, H. Du, and S. Sukhishvili, "In situ SERS study of Rhodamine 6G adsorbed on individually immobilized Ag nanoparticles," J. Raman Spec., 37(7):762, 2006.

D. J. White and P. R. Stoddart, "Nanostructured optical fiber with surface-enhanced Raman scattering functionality," Opt. Lett., 30(6):598, 2005.

C. Gu and C. Shi, "Surface-enhanced Raman sensors improve detection of dangerous agents," Laser Focus World, 97-101, Jan. 2009.

\* cited by examiner

FIBER BASED SERS SENSOR

I. BACKGROUND

The invention relates generally to the field of surface enhanced Raman scattering (SERS). More particularly, the invention relates to fiber based SERS sensors.

II. SUMMARY

In one respect, disclosed is a SERS sensor comprising: a fiber laser; a fiber comprising a first end and a second end, wherein the first end is coupled to the fiber laser and the second end is deposited with one or more metal nanoparticles; an in-line fiber grating integrated into the fiber between the first and the second end; a spectrometer configured to measure a spectrum produced by the in-line fiber grating; and a micro-processor configured to control the fiber laser and the spectrometer.

In another respect, disclosed is a SERS sensor comprising: a fiber laser; a fiber comprising a first end and a second end, wherein the first end is coupled to the fiber laser; a coreless fiber comprising a third end and a fourth end, wherein the third end is spliced to the second end and the fourth end is deposited with one or more metal nanoparticles; an in-line fiber grating integrated into the fiber between the first and the second end; a spectrometer configured to measure a spectrum produced by the in-line fiber grating; and a micro-processor configured to control the fiber laser and the spectrometer.

In one respect, disclosed is a method for enhanced SERS sensing, the method comprising: generating electromagnetic radiation from a fiber laser; coupling the electromagnetic radiation to a SERS sensor comprising: a fiber comprising a first end and a second end, wherein the first end is coupled to the fiber laser and the second end is deposited with one or more metal nanoparticles; an in-line fiber grating integrated into the fiber between the first and the second end; a spectrometer configured to measure a spectrum produced by the in-line fiber grating; and a micro-processor configured to control the fiber laser and the spectrometer; exciting one or more molecules adsorbed on the surface of the one or more metal nanoparticles to generate a Raman signal; coupling the Raman signal into the fiber; separating the Raman signal into its wavelength components with the in-line fiber grating; and measuring the wavelength components with the spectrometer.

In another respect, disclosed is a method for enhanced SERS sensing, the method comprising: generating electromagnetic radiation from a fiber laser; coupling the electromagnetic radiation to a SERS sensor comprising: a fiber comprising a first end and a second end, wherein the first end is coupled to the fiber laser; a coreless fiber comprising a third end and a fourth end, wherein the third end is spliced to the second end and the fourth end is deposited with one or more metal nanoparticles; an in-line fiber grating integrated into the fiber between the first and the second end; a spectrometer configured to measure a spectrum produced by the in-line fiber grating; and a micro-processor configured to control the fiber laser and the spectrometer; exciting one or more molecules adsorbed on the surface of the one or more metal nanoparticles to generate a Raman signal; coupling the Raman signal into the fiber; separating the Raman signal into its wavelength components with the in-line fiber grating; and measuring the wavelength components with the spectrometer.

Numerous additional embodiments are also possible.

III. BRIEF DESCRIPTION OF THE DRAWINGS

Other objects and advantages of the invention may become apparent upon reading the detailed description and upon reference to the accompanying drawings.

Figure 1:
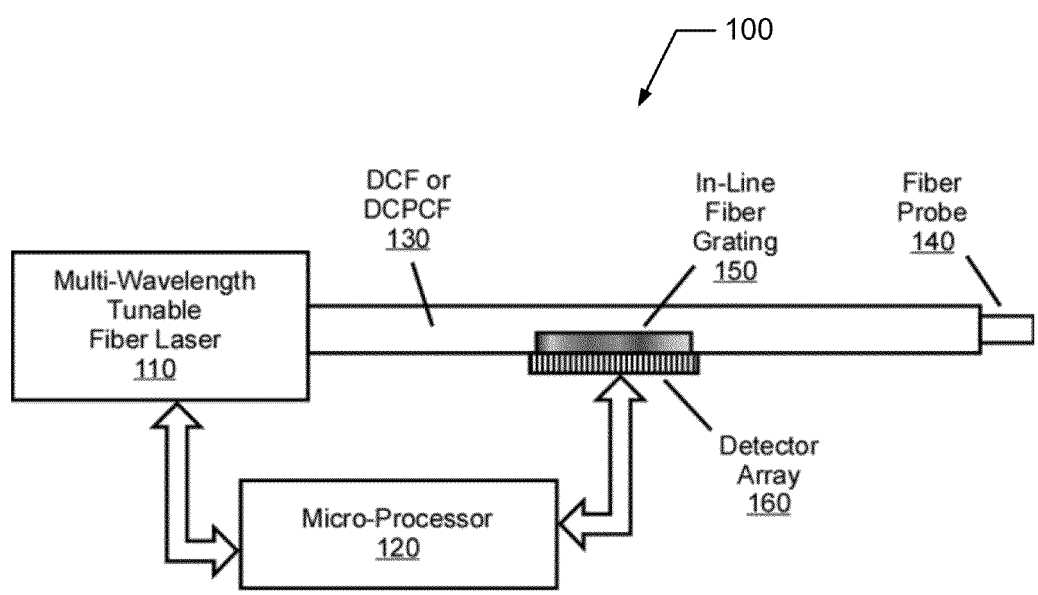
FIG. 1 is a schematic diagram of a multi-wavelength, all fiber SERS sensor system (M-SERS), in accordance with some embodiments.

While the invention is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

IV. DETAILED DESCRIPTION

One or more embodiments of the invention are described below. It should be noted that these and any other embodiments are exemplary and are intended to be illustrative of the invention rather than limiting. While the invention is widely applicable to different types of systems, it is impossible to include all of the possible embodiments and contexts of the invention in this disclosure. Upon reading this disclosure, many alternative embodiments of the present invention will be apparent to persons of ordinary skill in the art.

Raman scattering is an inelastic scattering process in which light is scattered off an excited molecule, which differs in frequency from the incident excitation beam. A change in polarization of the molecule must occur for the molecule to be Raman active. The vibrational energy levels of the molecule, which are governed by the molecule's structure and bond strengths, are determined by the frequency difference between the incident photon and the scattering photon. The ultimate outcome from this process is the "fingerprint" of the molecule, represented by the vibrational energies obtained by the Raman procedure. The main advantage of Raman scattering is its ability to provide high structural specificity since the unique frequency shift is distinctive to the probed molecule. Structures of complicated chemicals and some complex compound systems, such as biological materials, may also be analyzed. However, Raman signals can be relatively weak, which limits some of the practical applications for detection.

To make the Raman scattering effect practical, it is necessary to amplify the signal to detectable levels. In 1974, Fleischmann first observed that when molecules were attached to metal nanoparticles, the Raman signals can be enlarged by as much as $10^9$ times. This is called surface enhanced Raman scattering (SERS). SERS is mainly attributed to two effects. One is electromagnetic (EM) field enhancement which increases the electromagnetic field around the noble metal surface and the other is the chemical enhancement effect. For EM enhancement, the large electromagnetic fields on the surface of small (compared to the wavelength of light) metal particles result from the resonance of its surface electrons with the incident EM field. This phenomenon is known as surface plasmon resonance (SPR) and results in an enlarged electromagnetic field, which can come from either the excitation beam or the Raman scattered signal of the molecule. In this mechanism, calculations have shown an overall enhancement of the electric field, E, to approximately $E^4$. Larger enhancement can be observed when metal surface roughening or aggregation is taken into consideration. For SERS on roughened metal films, the enhancement is on the order of $10^3$-$10^5$. While isolated metal nanoparticles (NPs), primarily silver, have shown an enhancement of about $10^6$, NP aggregates have shown even stronger enhancement on the order of $10^7$-$10^9$. The increase in enhancement for aggregates is believed to be due to stronger field enhancement at the junctions of NPs or nanorods in the aggregates. Even larger SERS enhancement factors have been reported for single "hot" NPs or aggregates, on the order of $10^{15}$. These SERS enhancement studies suggest that NP aggregates are better for SERS than isolated NPs and that the Raman signal can be very large and easily detected. Therefore, nanoparticle aggregates address the small signal problem of standard Raman spectroscopy. Hence the main contributor to SERS is the amplification of the EM field which can interact with molecules adsorbed on the metal surface.

SERS sensors based on optical fibers demonstrate many merits in chemical and biological molecular specificity, high sensitivity, probe flexibility, low cost, ease of fabrication, and remote sensing. Fiber optics utilizes not only Raman scattered light as a sensing target but also absorbance, fluorescence, and SPR. Fiber optic sensors, based on SERS in particular, are generating exciting new advances in sensor technology. Spatial analysis with high resolution is possible using the fiber optic component probe. This spatial analysis capability allows fiber optic based sensors to chemically investigate at the single cell level. While SERS offers extremely large enhancement factors to increase the sensitivity of normal Raman which provides molecular specificity, optical fibers provide the robust and flexible probe to conduct detection in environmental and food safety, toxin detection, and military or security applications.

Since the first demonstration of fiber SERS sensors, several groups have been actively engaged in research on different fiber configurations. For example, T. Vo-Dinh's group has developed roughened optical fibers coated with silver on a flat tip for SERS detection, the silver islands-based SERS tapered fiber nanoprobe, and recently the fiber-optic nanosensors for single-cell monitoring. P. R. Stoddart's group has reported a roughened multimode fiber by acid etching to form densely packed microstructured cells, on which a layer of gold or silver thin film is deposited to form a SERS substrate. Microstructured optical fiber SERS probes have also been developed, for example the work by H. Du's group, where the silver deposition is obtained in the air cores in the microstructure as the SERS probe resulting in an enhancement factor of about $10^4$-$10^6$. Additionally, Viets' group has demonstrated angled configuration for fiber SERS probe, and Lucotti's group has reported a tapered fiber with high sensitivity. However, all these groups use CW lasers and free space components for laser coupling and spectrum analysis, which limits their practical applications. Since CW signal has low intensity, the enhancement factor is limited due to the SERS signal being proportional to $E^4$ of the optical field intensity.

The embodiment or embodiments described herein may solve these shortcomings as well as others by proposing a novel SERS system which includes a laser source with a spectral bandwidth less than 0.2 nm, a spectrometer (single detector with scanning optics or detector array based), and a fiber for delivery of light to the sample and collection of the Raman spectra from the sample.

FIG. 1 is a schematic diagram of a multi-wavelength, all fiber SERS sensor system (M-SERS), in accordance with some embodiments.

Figure 2:
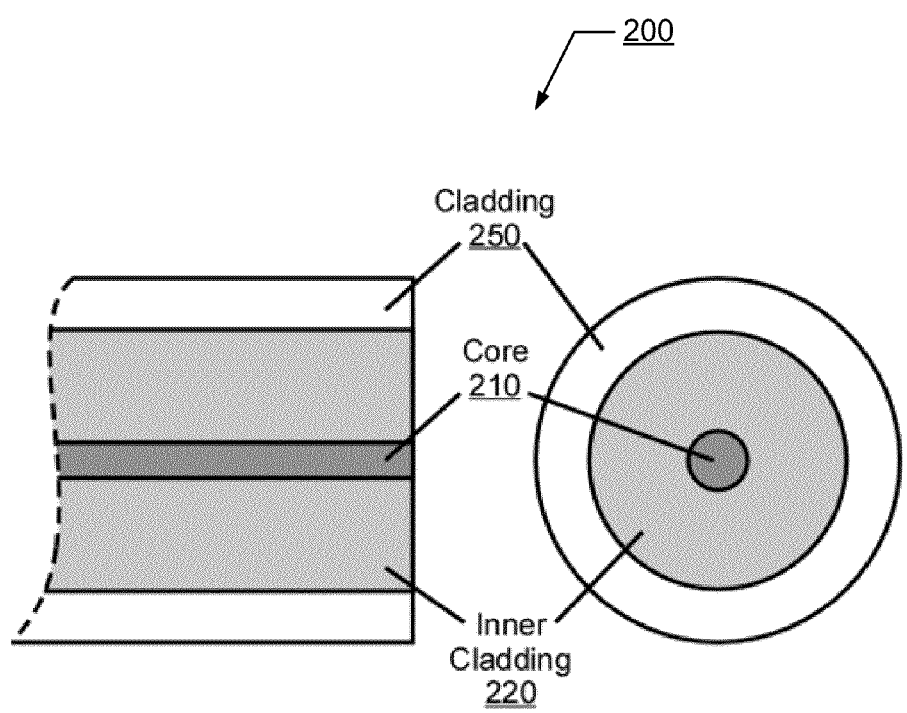
FIG. 2 is a schematic diagram of a double cladding fiber used in an M-SERS, in accordance with some embodiments.
Figure 3:
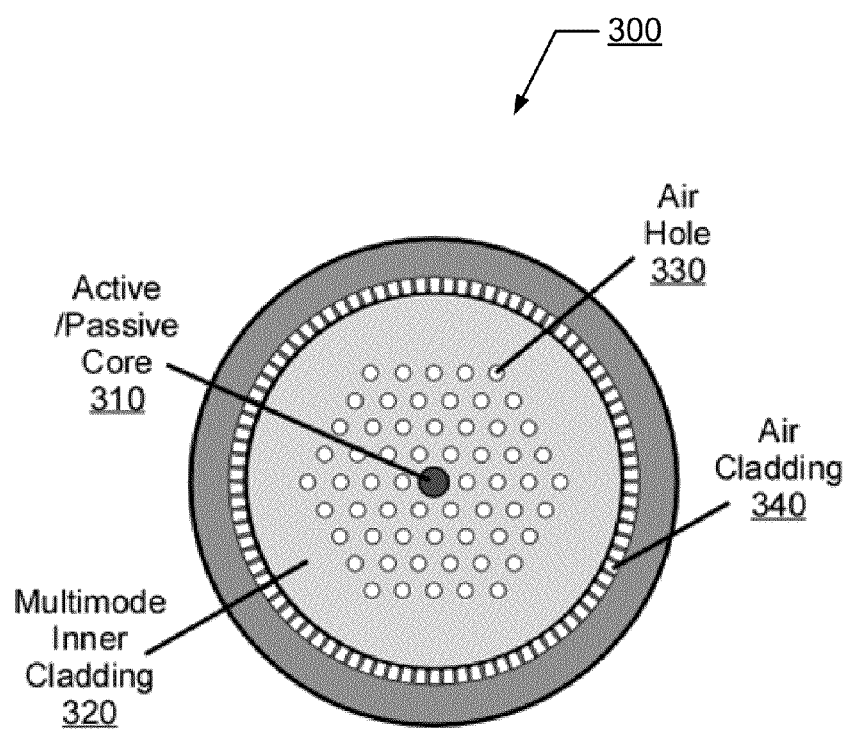
FIG. 3 is a schematic diagram of a double cladding photonic crystal fiber used in an M-SERS, in accordance with some embodiments.
Figure 4:
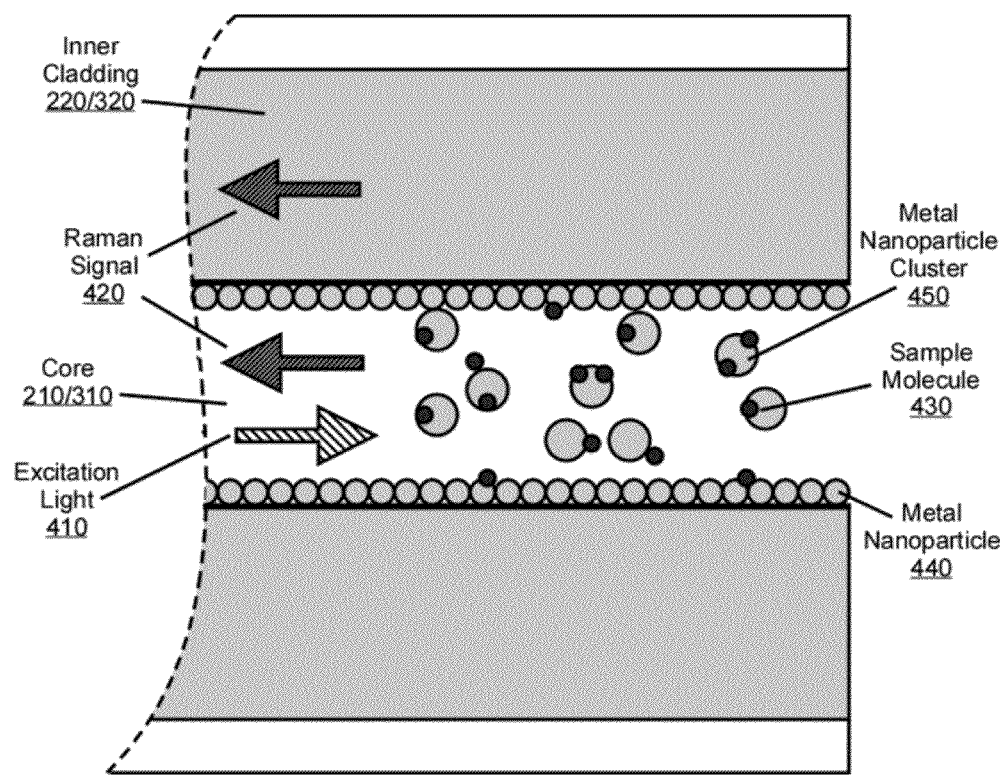
FIG. 4 is a diagram showing the generation of an enhanced Raman signal, in accordance with some embodiments.

In some embodiments, the all fiber SERS sensor system is based on a multi-wavelength excitation in a very compact form factor, for real time and in-situ characterization of low concentration chemical and bio agents at a vapor or liquid phase with high selectivity and sensitivity. The M-SERS system includes a wavelength tunable, ultrafast fiber laser 110 operating at 1030 nm, wavelength tunable up to 100 nm from 1010 nm to 1110 nm, and its second harmonic generation (SHG) wavelength of 515 nm, wavelength tunable up to 50 nm with a pulse width of picoseconds and peak power greater than 1 kW, and third/forth/fifth harmonic generation to UV (200-400 nm), a fiber based spectrometer, and a fiber probe 140. The fiber based spectrometer comprises an in-line fiber grating 150, a detector array 160 adjacent to the in-line fiber grating 150, and a micro-processor 120 to control and read from the detector array 160. Instead of using bulk, multi-element, free-space optics, a double cladding fiber 130, such as the double cladding fiber 200, as schematically illustrated in FIG. 2, or a double cladding photonic crystal fiber (DCPCF) 300, as schematically illustrated in FIG. 3 is used to compensate for group-velocity-dispersion and third-order dispersion. The double cladding fiber 200 of FIG. 2 comprises a cladding 250, an inner cladding 220, and a core 210. The double cladding photonic crystal fiber 300 of FIG. 3 comprises an active/passive core 310, a multimode inner cladding 320, air holes 330 within the multimode inner cladding 320, and an air cladding 340. The all fiber SERS sensor system functions, as illustrated in FIG. 4 by transferring laser excitation light 410 from the ultrafast fiber laser 110 down the core of the double cladding fiber 200 or the double cladding photonic crystal fiber 300 into the fiber probe 140. A surface enhanced Raman signal 420 is generated from the excited sample molecules 430 attached to the metal nanoparticles 440 and nanoparticle clusters 450 of the fiber probe 140 and then collected within the core 210 and the inner cladding 220 of the double cladding fiber 200 or the active/passive core 310 and the multimode inner cladding 320 of the double cladding photonic crystal fiber 300 and guided to the in-line fiber grating 150 where the Raman signal is separated into its wavelength components. A detector array 160, controlled by micro-processor 120, then measures the wavelength components of the Raman signal 420. From the measurements of the wavelength components of the Raman signal, the sample molecules 430 being probed can be identified. The metal nanoparticles 440 and nanoparticle clusters 450 include, but are not limited to, silver, nickel, aluminum, silicon, gold, platinum, palladium, titanium, copper, cobalt, zinc, other transition metals, composites thereof, oxides thereof, nitrides thereof, silicides thereof, phosphides ($P^{3-}$) thereof, oxynitrides thereof, carbides thereof, and combinations thereof. In particular the materials can include one or more of the following: silver, gold, nickel, silicon, germanium, silicon oxide, titanium oxide, and copper.

Figure 5:
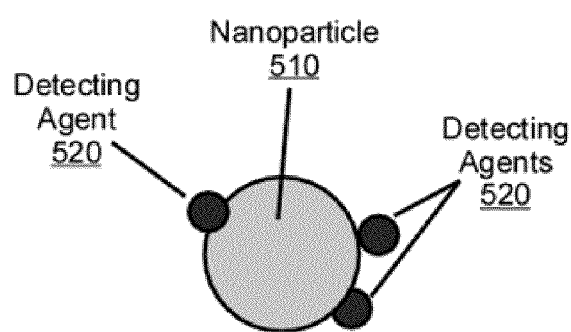
FIG. 5 is a schematic diagram showing a nanoparticle with an attached detecting agent, in accordance with some embodiments.
Figure 6:
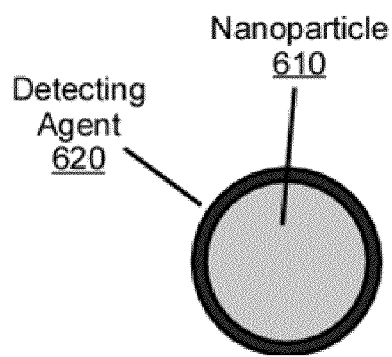
FIG. 6 is a schematic diagram showing a nanoparticle coated with a detecting agent, in accordance with some embodiments.

In some embodiments, depending on the application, a detecting agent may be attached to the metal nanoparticles and the metal nanoparticles clusters. FIG. 5 illustrates a nanoparticle 510 with attached detecting agents 520. FIG. 6 illustrates a nanoparticle 610 coated with a detecting agent 620. The detecting agents are used to capture or bind specific chemicals or compounds, for example, epidermal growth factor receptor (EGFR) binding to cancer cells.

Aside from advantages in miniaturization, a photonic crystal fiber has both normal and anomalous dispersion. Therefore, its structure can be tailored to compensate for both the nominal dispersion and the dispersion slope, providing optimal compensation over a larger spectral range. This embodiment provides ultra-short, less than 5 picoseconds, transform-limited pulse shape (spectral bandwidth <10 cm$^{-1}$), high peak intensity, greater than 1 kW pulses to the fiber probe 140. The inner cladding 220 may have a numerical aperture (NA) ranging from 0.2 to 0.8. The multimode inner cladding 320 of the DCPCF has a numerical aperture (NA) of greater than 0.6 to increase the collection of SERS signal. The embodiment of FIG. 1 provides superior properties with SERS enhancement of at least 1000 times higher, high signal to noise ratio (SNR), and miniaturization. For certain specific applications, a single fixed wavelength may be sufficient for SERS. Additionally, a pulse width between 1 to 200 nanoseconds may also be an alternative.

Figure 7:
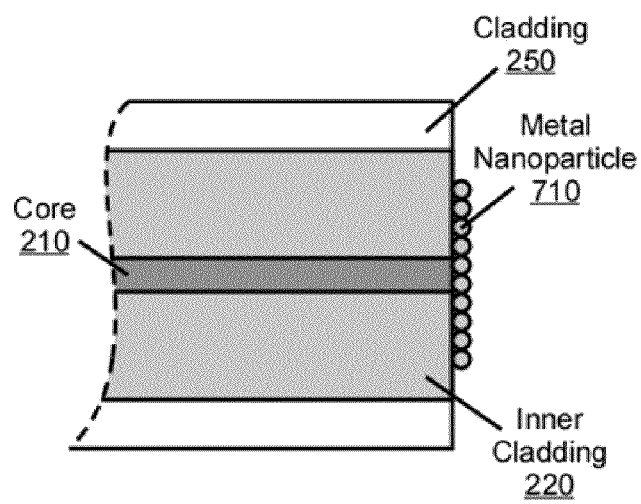
FIG. 7 is a schematic diagram of a fiber probe with deposited metal nanoparticles on a flat endface, in accordance with some embodiments.
Figure 8:
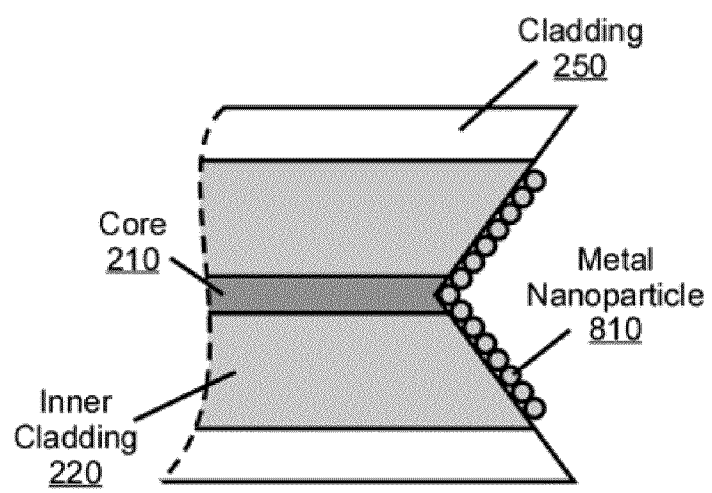
FIG. 8 is a schematic diagram of a fiber probe with deposited metal nanoparticles on a triangular endface, in accordance with some embodiments.
Figure 9:
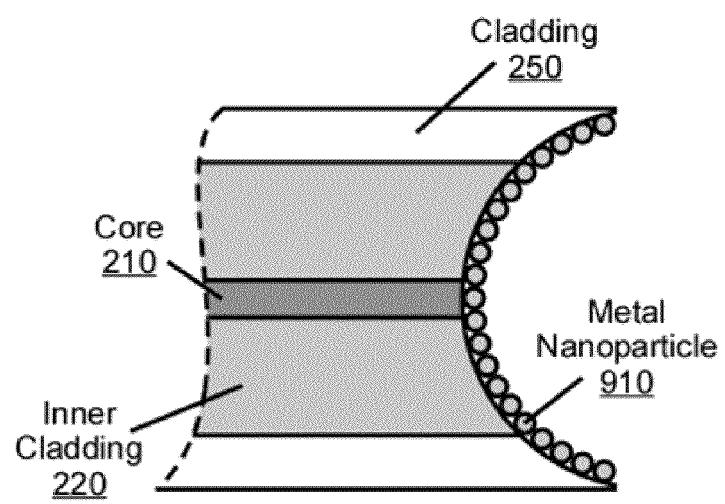
FIG. 9 is a schematic diagram of a fiber probe with deposited metal nanoparticles on a circular endface, in accordance with some embodiments.
Figure 10:
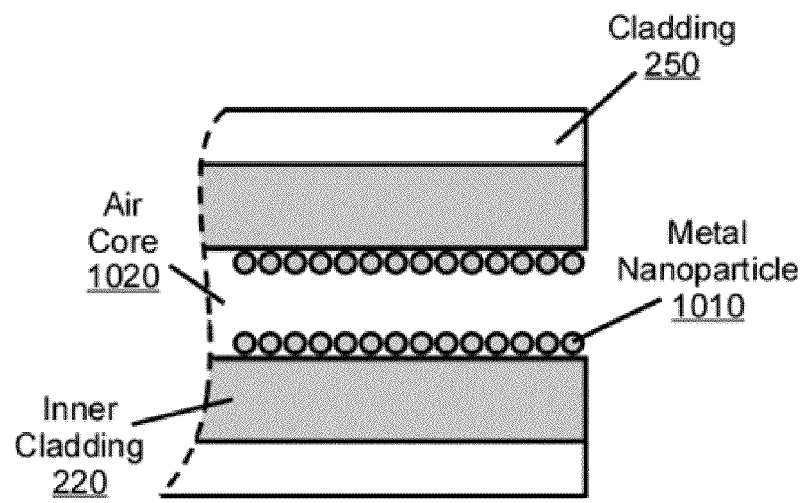
FIG. 10 is a schematic diagram of a fiber probe with deposited metal nanoparticles on the inner surface of the fiber probe air core, in accordance with some embodiments.

In some embodiments, the fiber for delivering excitation signal and collecting Raman signals is specially designed for enhanced Raman scattering. The fibers, as illustrated in FIGS. 7-10, all exhibit large enhancement factors. The fiber shapes include a flat end shape, a triangular end shape, a rectangular end shape, a circular end shape, a hollow core end shape, or any other arbitrary shape. As used here, the term "arbitrary" may refer to any end shape that results in an increased end surface area. The fiber may be processed through chemical etching or laser assisted material processing. The metal nanoparticles, such as gold, silver, copper, etc., can be deposited to the shaped surfaces through chemical (solution), electrical (e.g. ion sputtering deposition), or optical methods (coating, or laser assisted deposition). FIG. 7 illustrates a double cladding fiber probe with metal nanoparticles 710 deposited on a flat end surface. FIG. 8 illustrates a double cladding fiber probe with metal nanoparticles 810 deposited on a triangular end surface. FIG. 9 illustrates a double cladding fiber probe with metal nanoparticles 910 deposited on a circular end surface. FIG. 10 illustrates a double cladding fiber probe with metal nanoparticles 1010 deposited on the inner surface of the fiber probe air core 1020.

Figure 11:
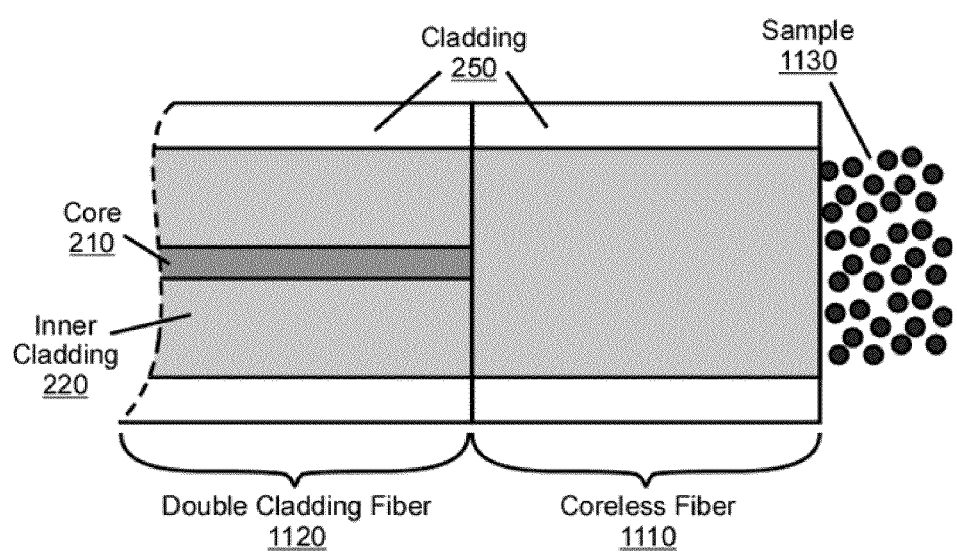
FIG. 11 is a schematic diagram of double cladding fiber spliced to a piece of coreless fiber, in accordance with some embodiments.

FIG. 11 is a schematic diagram of double cladding fiber spliced to a piece of coreless fiber, in accordance with some embodiments.

Figure 12:
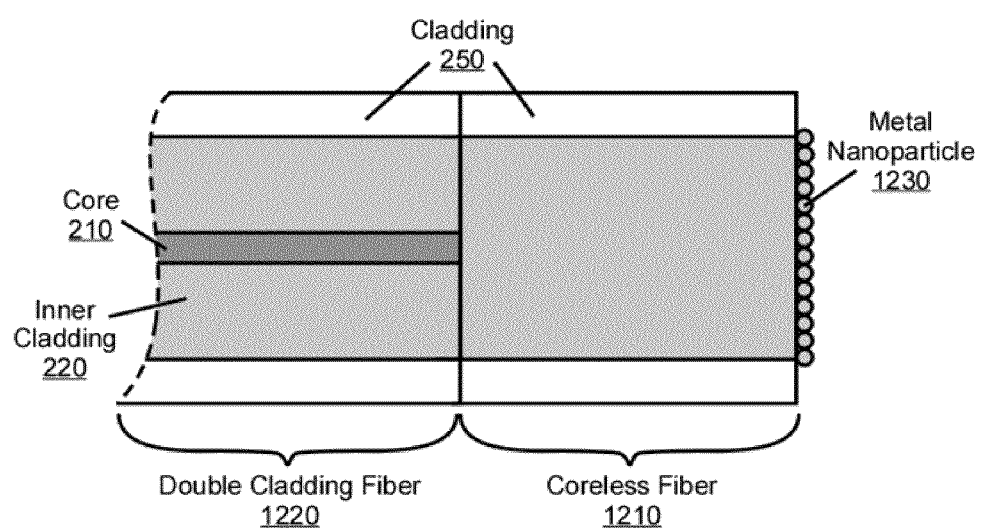
FIG. 12 is a schematic diagram of double cladding fiber spliced to a piece of coreless fiber with deposited metal nanoparticles on a flat endface, in accordance with some embodiments.
Figure 13:
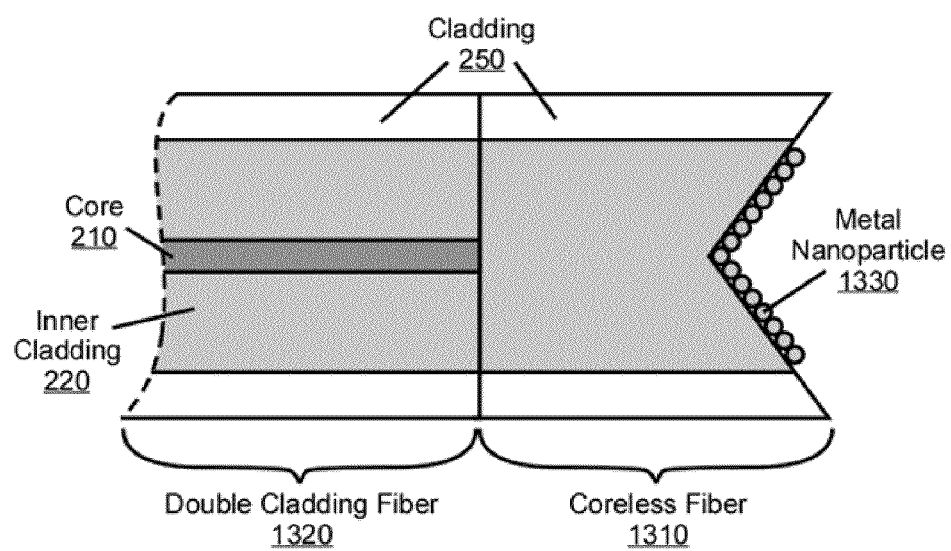
FIG. 13 is a schematic diagram of double cladding fiber spliced to a piece of coreless fiber with deposited metal nanoparticles on a triangular endface, in accordance with some embodiments.
Figure 14:
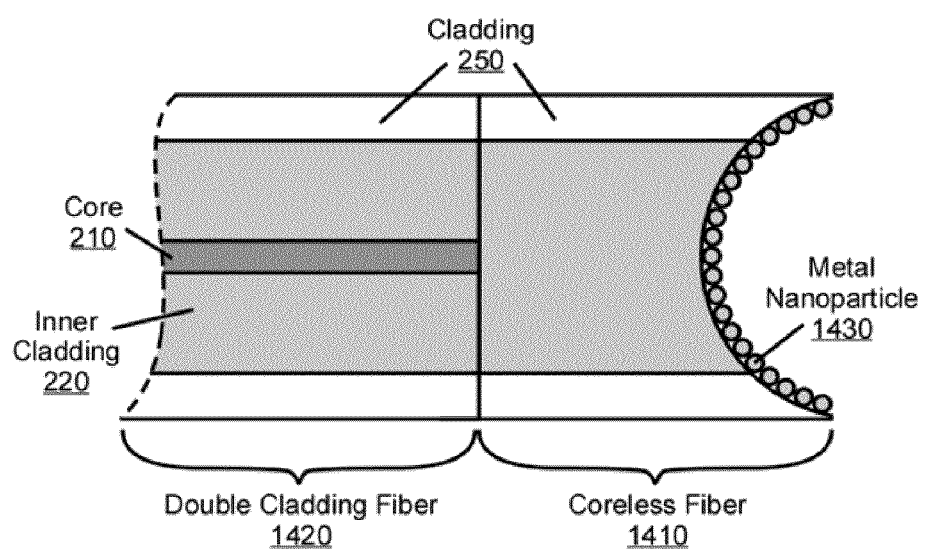
FIG. 14 is a schematic diagram of double cladding fiber spliced to a piece of coreless fiber with deposited metal nanoparticles on a circular endface, in accordance with some embodiments.

In some embodiments, a piece of coreless fiber 1110 is spliced to the double cladding fiber 1120. This results in the spreading of the excitation light signal into the cladding before reaching the sample 1130, resulting in an enhanced interaction area of Raman signal since the whole area of the fiber endface is utilized. The Raman signal is then collected through the double cladding fiber 1120 and detected by the spectrometer. The length of the coreless fiber 1110 spliced to the double cladding fiber 1120 ranges from approximately 0.5 mm to a few centimeters depending on the NA of the inner cladding of double cladding fiber 1120. Metal nanoparticles can also be deposited on the endface of the coreless fiber to enhance the Raman signal. Additionally, the endface of the coreless fiber can be shaped to provide additional Raman signal enhancement. FIGS. 12-14 illustrate double cladding fiber spliced to coreless fiber with various types of shaped end surfaces. FIG. 12 illustrates a flat end surface of coreless fiber 1210 spliced to a double cladding fiber 1220 where the flat end surface of coreless fiber has deposited metal nanoparticles 1230. FIG. 13 illustrates a triangular end surface of coreless fiber 1310 spliced to a double cladding fiber 1320 where the triangular end surface of coreless fiber has deposited metal nanoparticles 1330. FIG. 14 illustrates a circular end surface of coreless fiber 1410 spliced to a double cladding fiber 1420 where the circular end surface of coreless fiber has deposited metal nanoparticles 1430. In some embodiments, the double cladding fiber delivering the laser excitation to the probe region is a double cladding photonic crystal fiber as shown in FIG. 3. The fiber based SERS sensor with a double cladding photonic crystal fiber may also have similar fiber probe ends as shown in FIGS. 7-14.

In some embodiments, a gradient index (GRIN) fiber or lens with higher NA is spliced to the end of the double cladding fiber or double cladding photonic crystal fiber. This results in improved collection of the Raman signal as a result of the higher NA. Improved collection of the Raman signal increases the sensitivity of the fiber SERS sensor.

Figure 15:
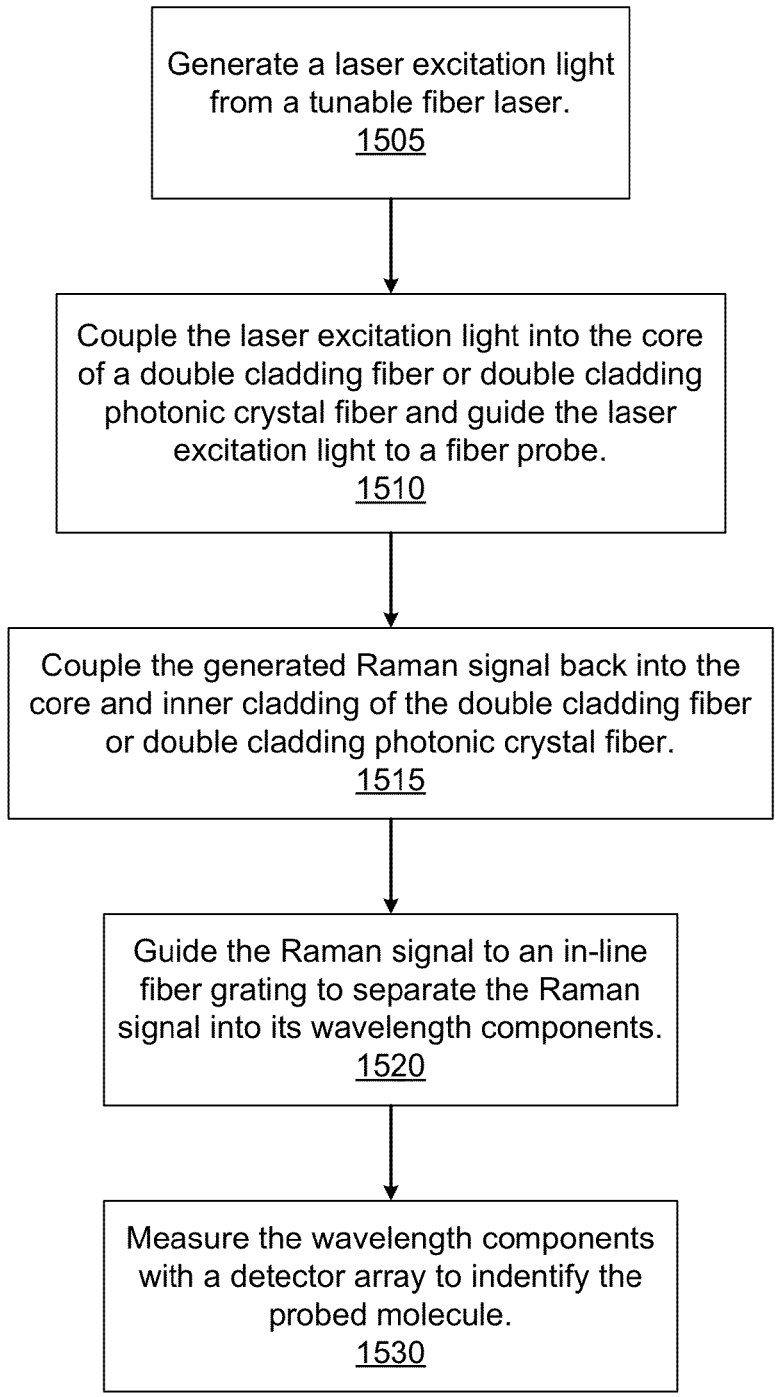
FIG. 15 is a block diagram illustrating a method for surface enhanced Raman scattering, in accordance with some embodiments.

FIG. 15 is a block diagram illustrating a method for surface enhanced Raman scattering, in accordance with some embodiments.

In some embodiments, a tunable fiber laser is used to generate a laser excitation light 1505. The tunable fiber laser may be a single wavelength or multi-wavelength tunable fiber laser. Additionally, the tunable fiber laser may be pulsed to further enhance the generated Raman signal. The laser excitation light is coupled into the core of a double cladding fiber or double cladding photonic crystal fiber and guided to a fiber probe 1510. The fiber probe is specially designed to enhance the Raman signal. The Raman signal is enhanced by deposited metal nanoparticles on the endface of the fiber probe. The endface may also be designed with different shapes, such as triangular and circular, to increase the interaction area between the laser excitation light and the molecules under investigation that are attached to the metal nanoparticles. The fiber probe may also have spliced to the end a segment of coreless fiber, with metal nanoparticles deposited on the endface of the coreless fiber, which also results in increased interaction area. The coreless fiber may also have a shaped endface to increase interaction area. The generated surface enhanced Raman signal is subsequently coupled back into the core and inner cladding of the double cladding fiber or double cladding photonic crystal fiber 1515. The Raman signal is guided to an in-line fiber grating where the Raman signal is separated into its wavelength components 1520. The wavelength components are measured with a detector array in order to identify the probed molecule 1530.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

The invention claimed is:

1. A SERS sensor comprising:
a fiber laser;
a fiber comprising a first end and a second end, wherein the first end is coupled to the fiber laser;
a coreless fiber comprising a third end and a fourth end, wherein the third end is spliced to the second end and the fourth end is deposited with one or more metal nanoparticles;
an in-line fiber grating integrated into the fiber between the first and the second end;
a spectrometer configured to measure a spectrum produced by the in-line fiber grating; and
a micro-processor configured to control the fiber laser and the spectrometer.

2. The SERS sensor of claim 1, wherein the fourth end comprises at least one of: a flat end shape, a triangular end shape, a rectangular end shape, a circular end shape, and any other arbitrary end shape.

3. The SERS sensor of claim 1, wherein the second end comprises a GRIN fiber or lens.

4. The SERS sensor of claim 1, wherein the fiber comprises a double cladding fiber or a double cladding photonic crystal fiber.

5. The SERS sensor of claim 1, wherein the one or more metal nanoparticles is at least one of: gold, silver, nickel, silicon, germanium, silicon oxide, titanium oxide, and copper.

6. The SERS sensor of claim 1, wherein the spectrometer comprises an array of detectors or a single detector with scanning optics.

7. The SERS sensor of claim 1, wherein the fiber laser operates at a single wavelength or multiple wavelengths and is configured to be tunable.

8. The SERS sensor of claim 1, wherein the fiber laser is configured to be pulsed.

9. The SERS sensor of claim 1, wherein a detecting agent is attached to the one or more metal nanoparticles.

10. The SERS sensor of claim 1, wherein a detecting agent is coated to the one or more metal nanoparticles.

11. A method for enhanced SERS sensing, the method comprising:
generating electromagnetic radiation from a fiber laser;
coupling the electromagnetic radiation to a SERS sensor comprising:
a fiber comprising a first end and a second end, wherein the first end is coupled to the fiber laser;
a coreless fiber comprising a third end and a fourth end, wherein the third end is spliced to the second end and the fourth end is deposited with one or more metal nanoparticles;
an in-line fiber grating integrated into the fiber between the first and the second end;
a spectrometer configured to measure a spectrum produced by the in-line fiber grating; and
a micro-processor configured to control the fiber laser and the spectrometer;
exciting one or more molecules adsorbed on the surface of the one or more metal nanoparticles to generate a Raman signal;
coupling the Raman signal into the fiber;
separating the Raman signal into its wavelength components with the in-line fiber grating; and
measuring the wavelength components with the spectrometer.

12. The method of claim 11, wherein the fourth end comprises at least one of: a flat end shape, a triangular end shape, a rectangular end shape, a circular end shape, a hollow core end shape, and any other arbitrary end shape.

13. The method of claim 11, wherein the second end comprises a GRIN fiber or lens.

14. The method of claim 11, wherein the fiber comprises a double cladding fiber or a double cladding photonic crystal fiber.

15. The method of claim 11, wherein the one or more metal nanoparticles is at least one of: gold, silver, nickel, silicon, germanium, silicon oxide, titanium oxide, and copper.

16. The method of claim 11, wherein the spectrometer comprises an array of detectors or a single detector with scanning optics.

17. The method of claim 11, wherein the fiber laser operates at a single wavelength or multiple wavelengths and is configured to be tunable.

18. The method of claim 11, wherein the fiber laser is configured to be pulsed.

19. The method of claim 11, wherein a detecting agent is attached to the one or more metal nanoparticles.

20. The method of claim 11, wherein a detecting agent is coated to the one or more metal nanoparticles.

* * * * *